(12) United States Patent
Tiwari et al.

(10) Patent No.: US 10,161,812 B2
(45) Date of Patent: Dec. 25, 2018

(54) THERMAL ANALYSIS OF ELECTRONICS RACKS

(71) Applicants: AIRBUS GROUP INDIA PRIVATE LIMITED, Bangalore (IN); AIRBUS OPERATIONS GMBH, Hamburg (DE)

(72) Inventors: Punit Tiwari, Bangalore (IN); Krishan Chugh, Bangalore (IN); Tim Giese, Hamburg (DE)

(73) Assignee: AIRBUS GROUP INDIA PRIVATE LIMITED, Banagalore, Karnataka (IN)

( * ) Notice: Subject to any disclaimer, the term of this patent is extended or adjusted under 35 U.S.C. 154(b) by 189 days.

(21) Appl. No.: 15/149,090

(22) Filed: May 7, 2016

(65) Prior Publication Data

US 2016/0327437 A1    Nov. 10, 2016

(30) Foreign Application Priority Data

May 7, 2015  (IN) ............................ 2331/CHE/2015

(51) Int. Cl.
*G01K 13/00*  (2006.01)
*G01N 25/18*  (2006.01)
*G06F 17/50*  (2006.01)

(52) U.S. Cl.
CPC ............. *G01K 13/00* (2013.01); *G01N 25/18* (2013.01); *G06F 17/5018* (2013.01); *G06F 2217/80* (2013.01)

(58) Field of Classification Search
CPC . G06F 17/5018; G06F 2217/80; G01K 13/00; G01N 25/18
See application file for complete search history.

(56) References Cited

U.S. PATENT DOCUMENTS

| | | | |
|---|---|---|---|
| 6,804,622 B2 * | 10/2004 | Bunker ................. | G01K 11/30 374/43 |
| 7,647,216 B2 * | 1/2010 | Bermejo Alvarez ........................ | G06F 17/5018 703/2 |
| 9,146,652 B1 * | 9/2015 | Danielsson ............. | G06F 3/048 |
| 2013/0060541 A1 * | 3/2013 | Mangat ............... | G06F 17/5018 703/2 |

* cited by examiner

*Primary Examiner* — Elias Desta
(74) *Attorney, Agent, or Firm* — Prakash Nama; Global IP Services, PLLC

(57) ABSTRACT

A technique for performing thermal analysis of an electronics rack is disclosed. In one embodiment, the electronics rack having multiple heat generating components is modeled. Further, thermal boundary conditions for each of the heat generating components are computed, by a computation fluid dynamics tool (CFD) tool, based on an initial temperature and a heat flux corresponding to each of the heat generating components in a first cycle, upon modeling the electronics rack. Furthermore, an actual temperature of each of the heat generating components is determined, by a one dimensional (1D) tool, using the computed thermal boundary conditions for estimating heat dissipated by each of the heat generating components in the first cycle.

16 Claims, 4 Drawing Sheets

THERMAL ANALYSIS OF ELECTRONICS RACKS

RELATED APPLICATIONS

Benefit is claimed under 35 U.S.C. 119(a)-(d) to Foreign Application Serial No. 2331/CHE/2015 filed in India entitled "THERMAL ANALYSIS OF ELECTRONICS RACKS", filed on May 7, 2015, by AIRBUS GROUP INDIA PRIVATE LIMITED and AIRBUS OPERATIONS GMBH which is herein incorporated in its entirety by reference for all purposes.

TECHNICAL FIELD

Embodiments of the present subject matter generally relate to thermal analysis, and more particularly, to thermal analysis of electronics racks.

BACKGROUND

Generally, thermal analysis of an electronics rack is performed to determine a temperature of each of multiple heat generating components in the electronics rack. Further, the temperature of each heat generating component may be used to determine whether heat dissipated by the heat generating components is within a predetermined threshold or not.

In an existing approach, thermal analysis of the electronics rack is performed using a one dimensional (1D) tool. In this approach, the temperature of each heat generating component is determined using algebraic equations. However, the 1D tool may rely on algebraic correlations and assume one or more variables in the algebraic equations. Thus, accuracy of the thermal analysis may be compromised and make the analysis unreliable.

In another existing approach, a three dimensional (3D) tool, such as a computation fluid dynamics (CFD) tool is used to perform the thermal analysis of the electronics rack. In this approach, detailed modeling of the electronics rack and the heat generating components is performed and the temperature of each of the heat generating components is then determined. However, detailed modeling of the electronics rack and the heat generating components may result in huge numerical grid cell count leading to significant increase in computation time and cost.

SUMMARY

A technique for performing thermal analysis of an electronics rack is disclosed. According to one aspect of the present subject matter, the electronics rack having multiple heat generating components is modeled. Further, thermal boundary conditions for each of the heat generating components are computed, by a computation fluid dynamics tool (CFD) tool, based on an initial temperature and a heat flux corresponding to each of the heat generating components in a first cycle, upon modeling the electronics rack. Furthermore, an actual temperature of each of the heat generating components is determined, by a one dimensional (1D) tool, using the computed thermal boundary conditions for estimating heat dissipated by each of the heat generating components in the first cycle.

According to another aspect of the present subject matter, the system includes a processor and a memory coupled to the processor. Further, the memory includes a mesh generation tool, a CFD tool and a 1D tool. In one embodiment, the mesh generation tool models the electronics rack having multiple heat generating components. Further, the CFD tool computes thermal boundary conditions for each of the heat generating components, upon modeling the electronics rack, based on an initial temperature and a heat flux corresponding to each of the heat generating components in a first cycle. The 1D tool then determines an actual temperature of each of the heat generating components using the computed thermal boundary conditions for estimating heat dissipated by each of the heat generating components in the first cycle.

According to yet another aspect of the present subject matter, a non-transitory computer-readable storage medium for performing thermal analysis of an electronics rack, having instructions that, when executed by a computing device causes the computing device to perform the method described above.

The system and method disclosed herein may be implemented in any means for achieving various aspects. Other features will be apparent from the accompanying drawings and from the detailed description that follow.

BRIEF DESCRIPTION OF THE DRAWINGS

Various embodiments are described herein with reference to the drawings, wherein.

Figure 1:
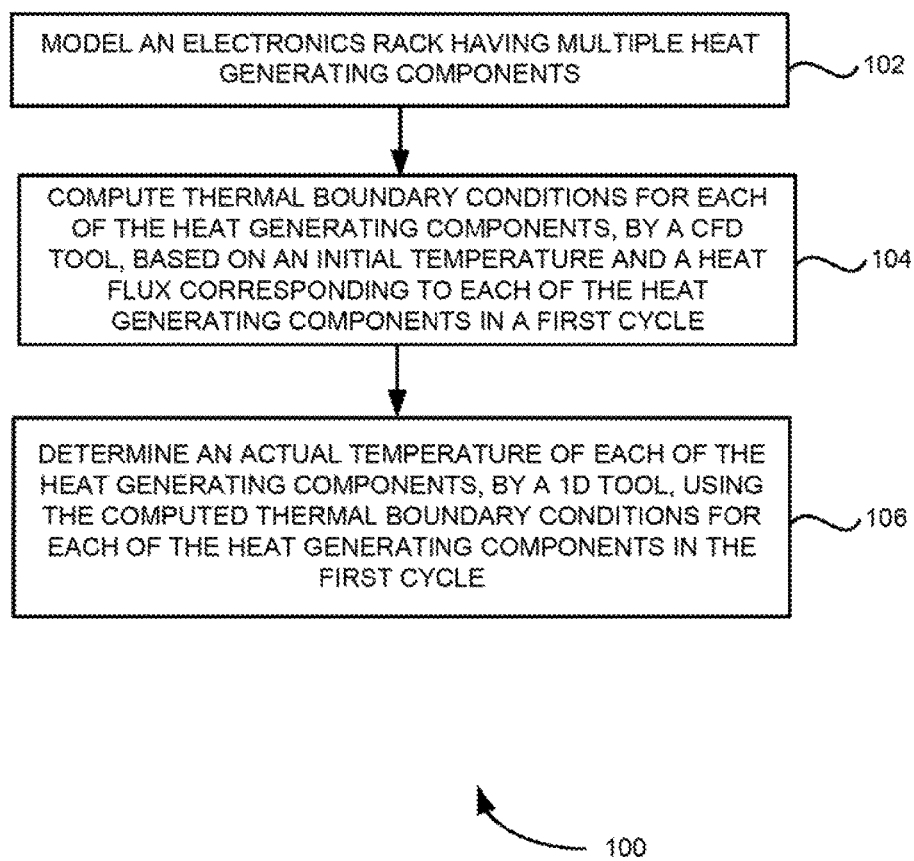
FIG. 1 is a flow diagram illustrating a method of performing thermal analysis of an electronics rack, according to one embodiment.

The drawings described herein are for illustration purposes only and are not intended to limit the scope of the present disclosure in any way.

DETAILED DESCRIPTION

In the following detailed description of the embodiments of the present subject matter, references are made to the accompanying drawings that form a part hereof, and in which are shown by way of illustration specific embodiments in which the present subject matter may be practiced. These embodiments are described in sufficient detail to enable those skilled in the art to practice the present subject matter, and it is to be understood that other embodiments may be utilized and that changes may be made without departing from the scope of the present subject matter. The following detailed description is, therefore, not to be taken in a limiting sense, and the scope of the present subject matter is defined by the appended claims.

Embodiments described herein provide methods, techniques, and systems for performing thermal analysis of an electronics rack having heat generating components. For example, the electronics rack can be in an avionics bay, a data centre, an equipments bay and the like. In this technique, a mesh generation tool models the electronics rack in a form of a rectangular bounding box or any other shape with interfaces of the heat generating components on outer surfaces of the bounding box. The mesh generation tool then creates one or more layers of a fluid volume mesh around the bounding box.

Further, a computational fluid dynamics (CFD) tool provides an initial temperature of each of the heat generating components, obtained from a one dimensional (1D) tool or user inputs or experimental values, as a temperature boundary condition on corresponding outer surfaces (i.e., on the interfaces or impressions of the heat generating components) in a first cycle. Furthermore, the CFD tool provides a net heat flux corresponding to the heat generating components as a net heat flux boundary condition to the fluid volume mesh in the first cycle. In addition, the CFD tool computes thermal boundary conditions of each of the heat generating components based on the associated temperature boundary condition and the net heat flux boundary condition in the first cycle. Moreover, the 1D tool determines an actual temperature of each of the heat generating components based on the thermal boundary conditions for estimating heat dissipated by each of the heat generating components in the first cycle. In some embodiments, the process steps of computing the thermal boundary conditions and determining the actual temperature of each of the heat generating components are continued for a predefined number of cycles or until there is no change in the temperature boundary condition and the net heat flux boundary condition (i.e., until convergence occurs). In this technique, the CFD tool and 1D tool are used for performing thermal analysis of the electronics rack. Thus, this technique may be reliable and not require detailed modelling of the electronics rack leading to reduction in computation time and cost.

Figure 2:
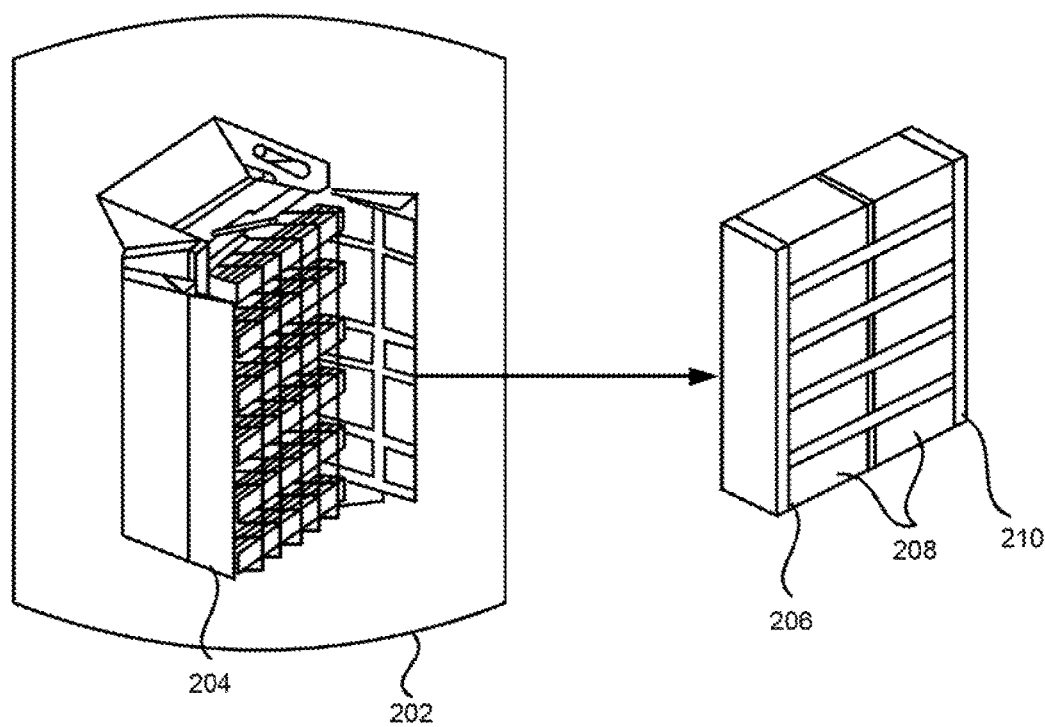
FIG. 2 is a schematic diagram illustrating an electronics rack and a bounding box created around the electronics rack, according to one embodiment.

FIG. 1 is a flow diagram 100 illustrating a method of performing thermal analysis of an electronics rack, according to one embodiment. For example, the electronics rack can be in an avionics bay, a data centre and the like. At block 102, the electronics rack having multiple heat generating components (e.g., an electronics rack 204 in an equipments bay 202 of FIG. 2) is modeled by a mesh generation tool. In an embodiment, a bounding box (e.g., a bounding box 206 shown in FIG. 2) is created around the electronics rack having interfaces (e.g., interfaces 208 of FIG. 2) representing each of the heat generating components, by the mesh generation tool. For example, the bounding box can be of any shape depending on geometry of the electronics rack. Further in this embodiment, one or more layers of a fluid volume mesh (e.g., a fluid volume mesh 210 of FIG. 2) are created, by the mesh generation tool, around the created bounding box. An example schematic diagram 200 shown in FIG. 2 illustrates the electronics rack 204 in the equipments bay 202 and the bounding box 206 created around the electronics rack 204 using the mesh generation tool. The remaining volume of the electronics rack is then meshed by a CFD tool.

At block 104, thermal boundary conditions for each of the heat generating components are computed, by the CFD tool, based on an initial temperature and a heat flux corresponding to each of the heat generating components in a first cycle, upon modeling the electronics rack. For example, the thermal boundary conditions include a heat transfer co-efficient and a reference temperature. In an example, a reference temperature of a heat generating component is a temperature of air in the vicinity of the heat generating component. In an embodiment, the initial temperature of each of the heat generating components is provided as a temperature boundary condition to the corresponding interface in the bounding box by the CFD tool. The initial temperature of each of the heat generating components is obtained from a 1D tool or user inputs or experimental values. Further, a net heat flux corresponding to the heat generating components is provided, by the CFD tool, as a net heat flux boundary condition to the fluid volume mesh. The net heat flux corresponding to the heat generating components is obtained based on associated design configuration of the heat generating components. The thermal boundary conditions for each of the heat generating components are then computed, by the CFD tool, based on the associated temperature boundary condition and the net heat flux boundary condition in the first cycle.

At block 106, an actual temperature of each of the heat generating component is determined, by the 1D tool, using the computed thermal boundary conditions of associated heat generating component for estimating heat dissipated by each of the heat generating components in the first cycle. In an example, the actual temperature of each of the heat generating components is determined using a below equation:

$$Q = A*H*(T_{equip} - T_{ref})$$

wherein,

Q is a heat transfer rate from a surface of a heat generating component,

H is a heat transfer co-efficient,

A is an area of the heat generating component, $T_{ref}$ is a reference temperature of the heat generating component, and $T_{equip}$ is the actual temperature of the heat generating component.

In some embodiments, the process steps of blocks 104 and 106 are repeated for a predefined number of cycles or until there is no change in the temperature boundary condition and the net heat flux boundary condition (i.e., until convergence occurs) using the determined actual temperature of each of the heat generating components in the first cycle.

Figure 3:
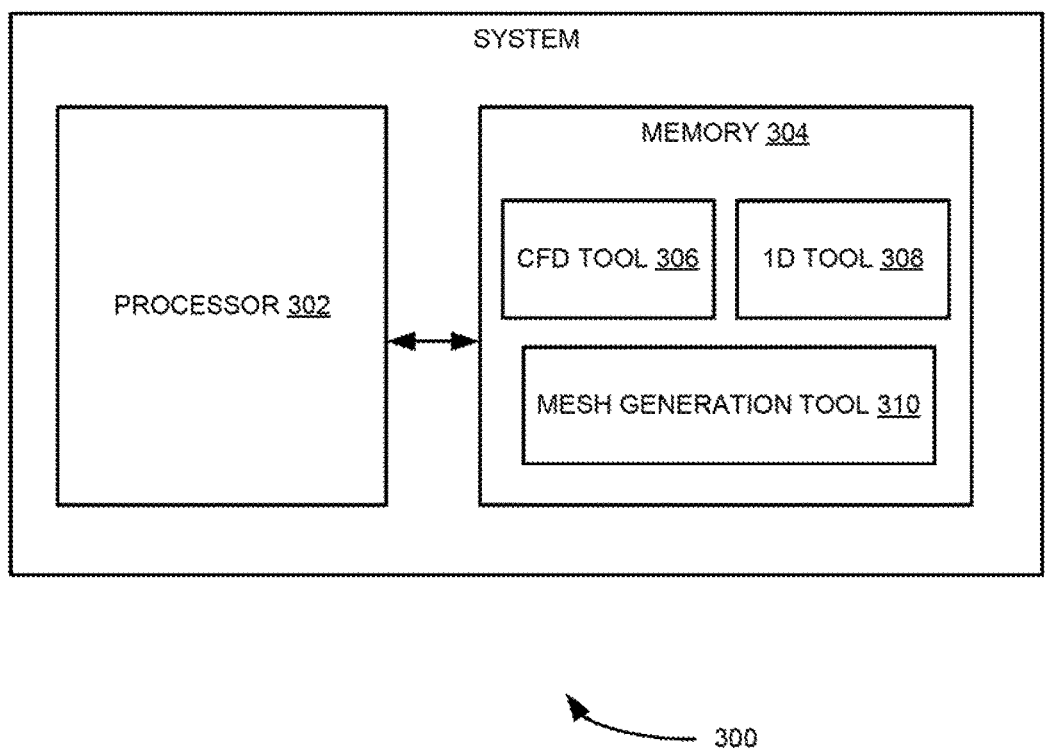
FIG. 3 illustrates a block diagram of a system for performing thermal analysis of an electronics rack, using the process described with reference to FIG. 1, according to one embodiment.

Referring now to FIG. 3, which illustrates a block diagram of a system 300 for performing thermal analysis of an electronics rack, using the process described with reference to FIG. 1, according to one embodiment. As shown in FIG. 3, the system 300 includes a processor 302 and a memory 304 communicatively coupled to the processor 302. Further, the memory 304 includes a CFD tool 306, a 1D tool 308 and a mesh generation tool 310.

In operation, the mesh generation tool 310 models the electronics rack having multiple heat generating components. For example, the electronics rack can be in an avionics bay, a data centre and the like. In an embodiment, the mesh generation tool 310 creates a bounding box around the electronics rack with interfaces representing each of the heat generating components. Further in this embodiment, the mesh generation tool 310 creates one or more layers of a fluid volume mesh around the created bounding box.

Further, the CFD tool 306 computes thermal boundary conditions for each of the heat generating components based on an initial temperature and a heat flux corresponding to each of the heat generating components in a first cycle. For example, the thermal boundary conditions include a heat transfer co-efficient and a reference temperature. In an example embodiment, the CFD tool 306 provides the initial temperature of each of the heat generating components as a temperature boundary condition to the corresponding interface in the bounding box. The CFD tool 306 then provides a net heat flux corresponding to the heat generating components as a net heat flux boundary condition to the one or more layers of the fluid volume mesh. The CFD tool 306 then computes the thermal boundary conditions for each of the heat generating components based on the associated temperature boundary condition and the net heat flux boundary condition in the first cycle.

Furthermore, the 1D tool 308 determines an actual temperature of each of the heat generating components using the computed thermal boundary conditions of the associated heat generating component for estimating heat dissipated by each of the heat generating components in the first cycle. In an example, the 1D tool determines the actual temperature of each of the heat generating components using a below equation:

$$Q=A*H*(T_{equip}-T_{ref})$$

wherein,
Q is a heat transfer rate from a surface of a heat generating component,
H is a heat transfer co-efficient,
A is an area of the heat generating component,
$T_{ref}$ is a reference temperature of the heat generating component, and
$T_{equip}$ is the second temperature of the heat generating component.

Also, the CFD tool 306 repeats the step of computing thermal boundary conditions for each of the heat generating components using the actual temperature, determined in the first cycle, in a next cycle. The 1D tool 308 then repeats the step of determining an actual temperature of each of the heat generating components, in the next cycle, based on the thermal boundary conditions. This process is continued until convergence occurs. This is explained in more detailed with reference to FIG. 1.

Figure 4:
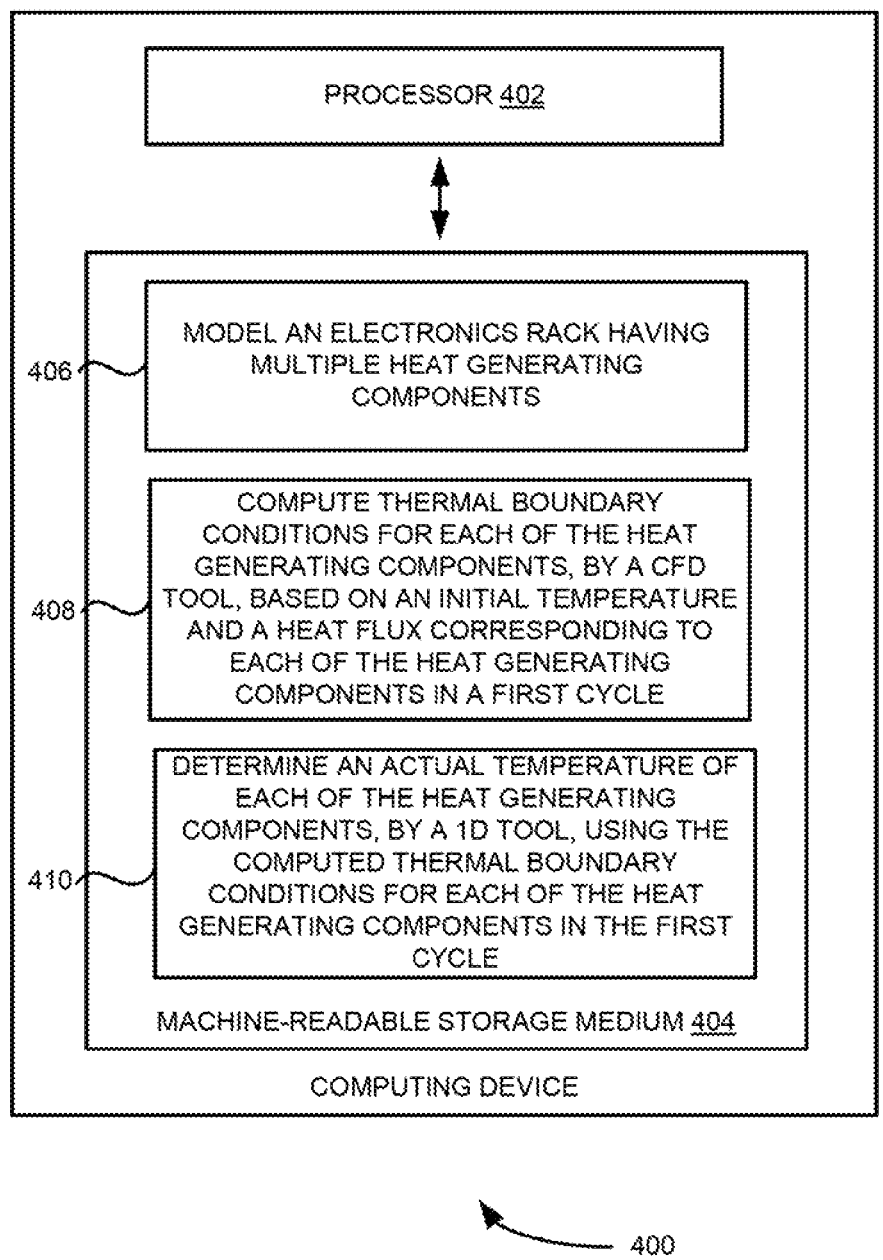
FIG. 4 illustrates a block diagram of a computing device for performing thermal analysis of an electronics rack, using the process described with reference to FIG. 1, according to one embodiment.

FIG. 4 is a block diagram of an example computing device 400 for performing thermal analysis of an electronics rack, using the process described with reference to FIG. 1, according to one embodiment. The computing device 400 includes a processor 402 and a machine-readable storage medium 404 communicatively coupled through a system bus. The processor 402 may be any type of central processing unit (CPU), microprocessor, or processing logic that interprets and executes machine-readable instructions stored in the machine-readable storage medium 404. The machine-readable storage medium 404 may be a random access memory (RAM) or another type of dynamic storage device that may store information and machine-readable instructions that may be executed by the processor 402. For example, the machine-readable storage medium 404 may be synchronous DRAM (SDRAM), double data rate (DDR), rambus DRAM (RDRAM), rambus RAM, etc., or storage memory media such as a floppy disk, a hard disk, a CD-ROM, a DVD, a pen drive, and the like. In an example, the machine-readable storage medium 404 may be a non-transitory machine-readable storage medium. In an example, the machine-readable storage medium 404 may be remote but accessible to the computing device 400.

The machine-readable storage medium 404 may store instructions 406, 408, and 410. In an example, instructions 406 may be executed by processor 402 to model the electronics rack having multiple heat generating components. Instructions 408 may be executed by processor 402 to compute thermal boundary conditions for each of the heat generating components, by a CFD tool upon modeling the electronics rack, based on an initial temperature and a heat flux corresponding to each of the heat generating components, in a first cycle. Instructions 410 may be executed by processor 402 to determine an actual temperature of each of the heat generating components, by a 1D tool, using the computed thermal boundary conditions for estimating heat dissipated by each of the heat generating components in the first cycle.

For the purpose of simplicity of explanation, the example method of FIG. 1 is shown as executing serially, however it is to be understood and appreciated that the present and other examples are not limited by the illustrated order. The example systems of FIGS. 3 and 4, and method of FIG. 1 may be implemented in the form of a computer program product including computer-executable instructions, such as program code, which may be run on any suitable computing device in conjunction with a suitable OS. Examples within the scope of the present disclosure may also include program products comprising non-transitory computer-readable storage media for carrying or having computer-executable instructions or data structures stored thereon. Such computer-readable media can be any available media that can be accessed by a general purpose or special purpose computer. By way of example, such computer-readable media can comprise RAM, ROM, EPROM, EEPROM, CD-ROM, magnetic disk storage or other storage devices, or any other medium which can be used to carry or store desired program code in the form of computer-executable instructions and which can be accessed by a general purpose or special purpose computer. The computer readable instructions can also be accessed from memory and executed by a processor.

Even though, in the above embodiments, the temperature of each of the heat generating components is determined, one can envision that the temperature of one or more of the heat generating components can be determined.

Although certain methods, systems, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

What is claimed is:
1. A method comprising:
  modeling an electronics rack having multiple heat generating components, comprising:
    creating a bounding box around the electronics rack with interfaces representing the heat generating components; and
    creating at least one layer of a fluid volume mesh around the created bounding box by a mesh generation tool;
  computing thermal boundary conditions for each of the heat generating components, by a computational fluid dynamics (CFD) tool, based on an initial temperature and a heat flux corresponding to each of fhe heat venerating components in a first cycle, upon modeling the electronics rack;
  determining actual temperature of each of the heat generating components, by a one dimensional (1D) tool, using the computed thermal boundary conditions in the first cycle; and
  controlling heat dissipated by each of the heat generating components based on the actual temperature of each of the heat generating components.
2. The method of claim 1, wherein computing the thermal boundary conditions for each of the heat generating components, by the CFD tool, based on the initial temperature and the heat flux corresponding to each of the heat generating components in the first cycle, comprises:

providing the initial temperature of a heat generating component as a temperature boundary condition to a corresponding interface in the bounding box, by the CFD tool;
providing a net heat flux corresponding to the heat generating components as a net heat flux boundary condition to the at least one layer of the fluid volume mesh, by the CFD tool; and
computing the thermal boundary conditions for the heat generating component, by the CFD tool, based on the temperature boundary condition and the net heat flux boundary condition in the first cycle.

3. The method of claim 1, wherein the thermal boundary conditions comprise a heat transfer co-efficient and a reference temperature.

4. The method of claim 3, whereinthe actual temperature of each of the heat generating components is determined, by the 1D tool, using a below equation:

$$Q=A*H*(T_{equip}-T_{ref})$$

wherein,
Q is a heat transfer rate from a surface of a heat generating component,
H is a heat transfer co-efficient,
A is an area of the heat generating component,
$T_{ref}$ is a reference temperature of the heat generating component, and
$T_{equip}$ is the actual temperature of the heat generating component.

5. The method of claim 1, further comprising:
repeating the steps of computing the thermal boundary conditions for each of the heat generating components using the actual temperature determined in the first cycle and determining an actual temperature of each of the heat generating components using the computed thermal boundary conditions for a predefined number of cycles.

6. A system, comprising:
a processor; and
a memory coupled to the processor, wherein the memory comprises:
a mesh generation tool to:
model an electronics rack having multiple heat generating components by:
creating a bounding box around the electronics rack with interfaces representing the beat generating components; and
creating at least one layer of a fluid volume mesh around the created bounding box;
a computational fluid dynamics (CFD) tool to:
compute thermal boundary conditions for each of the heat generating components, upon modeling the electronics rack, based on an initial temperature and a heat flux corresponding to each of the heat generating components in a first cycle; and
a one dimensional (1D) tool to:
determine an actual temperature of each of the heat generating components using the computed thermal boundary conditions in the first cycle, wherein the actual temperature of each of the heat generating components is used to control heat dissipated by each of the heat generating components.

7. The system of claim 6, wherein the CFD tool is configured to:
provide the initial temperature of a heat generating component as a temperature boundary condition to a corresponding interface in the bounding box;
provide a net heat flux corresponding to the heat generating components as a net heat flux boundary condition to the at least one layer of the fluid volume mesh; and compute the thermal boundary conditions for the heat generating component based on the temperature boundary condition and the net heat flux boundary condition in the first cycle.

8. The system of claim 6, wherein the thermal boundary conditions comprise a heat transfer co-efficient and a reference temperature.

9. The system of claim 8, wherein the 1D tool determines the actual temperature of each of the heat generating components using a below equation:

$$Q=A*H*(T_{equip}-T_{ref})$$

wherein,
Q a heat transfer rate from a surface of a heat generating component,
H is a heat transfer co-efficient,
A is an area of the heat generating component,
$T_{ref}$ is a reference temperature of the heat generating component, and
$T_{equip}$ is the actual temperature of the heat generating component.

10. The system of claim 6, wherein the CFD tool is further configured to:
compute the thermal boundary conditions for each of the heat generating components using the actual temperature, determined in the first cycle, in a next cycle.

11. The system of claim 10, wherein the 1D tool is further configured to:
determine an actual temperature of each of the heat generating components using the computed thermal boundary conditions in the next cycle.

12. A non-transitory computer-readable storage medium including instructions executable by a processor to:
model an electronics rack having multiple heat generating components by:
creating a hounding box around the electronics rack with interfaces representing the heat generating components; and
creating at least one layer of a fluid volume mesh around the created bounding box, by a mesh generation tool;
compute thermal boundary conditions for each of the heat generating components, by a computational fluid dynamics (CFD) tool, based on an initial temperature and a heat flux corresponding to each of the heat generating components in a first cycle, upon modeling the electronics rack;
determine an actual temperature of each of the heat generating components, by a one dimensional (1D) tool, using the computed thermal boundary conditions in the first cycle; and
controlling heat dissipated by each of the heat generating components based on the actual temperature of each of the heat generating components.

13. The non-transitory computer-readable storage medium of claim 12, wherein computing the thermal boundary conditions for each of the heat generating components, by the CFD tool, based on the initial temperature and the heat flux corresponding to each of the heat generating components in the first cycle, comprises:
providing the initial temperature of a heat generating component as a temperature boundary condition to a corresponding interface in the bounding box, by the CFD tool;
providing a net heat flux corresponding to the heat generating components as a net heat flux boundary condition to the at least one layer of the fluid volume mesh, by the CFD tool; and
computing the. thermal boundary conditions for the heat get erating component, by the CFD tool, based on the temperature boundary condition and the net beat flux boundary condition in the first cycle.

14. The non-transitory computer-readable storage medium of claim 12, wherein the thermal boundary conditions comprise a heat transfer co-efficient and a reference temperature.

15. The non-transitory computer-readable storage medium of claim 14, wherein the actual temperature of each of the heat generating components is determined using a below equation:

$$Q = A * H * (T_{equip} - T_{ref})$$

wherein,

Q is a heat transfer rate from a surface of a heat generating component,

H is a heat transfer co-efficient,

A is an area of the heat generating component.

$T_{ref}$ is a reference temperature of the heat generating component, and $T_{equip}$ is the actual temperature of the heat generating component.

16. The non-transitory computer-readable storage medium of claim 12, further comprising:

repeating the steps of computing the thermal boundary conditions for each of the heat generating components using the actual temperature determined in the first cycle and determining an actual temperature of each of the heat generating components using the computed thermal boundary conditions for a predefined number of cycles.

\* \* \* \* \*